United States Patent
Feletti et al.

(10) Patent No.: US 9,918,636 B2
(45) Date of Patent: Mar. 20, 2018

(54) SYSTEM FOR SIGNALLING DANGER WARNINGS ARISING FROM EXPOSURE OF A SUBJECT TO ATMOSPHERIC POLLUTANTS, AND CORRESPONDING METHOD AND MOBILE DEVICE

(71) Applicant: Universita degli Studi di Torino, Turin (IT)

(72) Inventors: Luca Carlo Feletti, Turin (IT); Luca Ferreri, Turin (IT); Marco Iacuaniello, Turin (IT); Marco Ivaldi, Turin (IT); Alberto Rainoldi, Turin (IT); Marco Turturici, Turin (IT)

(73) Assignee: UNIVERSITÀ DEGLI STUDI DI TORINO, Turin (IT)

( * ) Notice: Subject to any disclaimer, the term of this patent is extended or adjusted under 35 U.S.C. 154(b) by 82 days.

(21) Appl. No.: 14/760,369

(22) PCT Filed: Jan. 9, 2014

(86) PCT No.: PCT/IB2014/058155
§ 371 (c)(1),
(2) Date: Jul. 10, 2015

(87) PCT Pub. No.: WO2014/108851
PCT Pub. Date: Jul. 17, 2014

(65) Prior Publication Data
US 2015/0356851 A1    Dec. 10, 2015

(30) Foreign Application Priority Data

Jan. 11, 2013   (IT) .............................. TO2013A0022

(51) Int. Cl.
*G01D 21/00*       (2006.01)
*A61B 5/00*        (2006.01)
(Continued)

(52) U.S. Cl.
CPC ............ *A61B 5/0002* (2013.01); *G08B 21/12* (2013.01); *G08B 25/08* (2013.01); *G08B 25/10* (2013.01);
(Continued)

(58) Field of Classification Search
CPC ...................................................... G08B 21/12
(Continued)

(56) References Cited

U.S. PATENT DOCUMENTS

2010/0253509 A1    10/2010  Fu et al.
2011/0140913 A1*   6/2011   Montenero ........ G08B 21/0233
                                             340/870.07
(Continued)

FOREIGN PATENT DOCUMENTS

EP             1209886 A2      5/2002

OTHER PUBLICATIONS

Notification of Transmittal of the International Search Report and the Written Opinion of the International Searching Authority, or the Declaration, dated Mar. 27, 2014, per International Application No. PCT/IB2014/058155.

*Primary Examiner* — Brent Swarthout
(74) *Attorney, Agent, or Firm* — Heslin Rothenberg Farley & Mesiti P.C.; Victor A. Cardona, Esq.

(57) ABSTRACT

A system for signalling danger warnings arising from exposure of a subject to atmospheric pollutants, includes means for detecting environmental information in the proximity of the subject, and at least one personal mobile terminal. Sensor means are associated to the subject and configured for detecting one or more physiological parameters of the subject and supplying them to the personal mobile terminal. The system includes means for detecting the position of the subject and a data-processing module. The mobile terminal is configured for sending to the module local-detection data.

(Continued)

The terminal is configured for receiving from the module danger warnings arising from exposure to pollutants calculated in the module and displaying to the subject the danger warnings or issuing alarms as a function of the values of the aforesaid danger warnings.

14 Claims, 5 Drawing Sheets

(51) Int. Cl.
  *H04W 4/02*   (2018.01)
  *G08B 25/10*   (2006.01)
  *G08B 27/00*   (2006.01)
  *G08B 21/12*   (2006.01)
  *G08B 25/08*   (2006.01)
  *H04M 1/725*   (2006.01)
  *A61B 5/11*   (2006.01)
  *G01N 15/00*   (2006.01)

(52) U.S. Cl.
  CPC ........... *G08B 27/00* (2013.01); *G08B 27/006* (2013.01); *H04M 1/7253* (2013.01); *H04M 1/72538* (2013.01); *H04W 4/023* (2013.01); *A61B 5/1112* (2013.01); *A61B 5/681* (2013.01); *A61B 2560/0242* (2013.01); *G01N 2015/0046* (2013.01); *H04M 2250/10* (2013.01); *H04M 2250/12* (2013.01)

(58) Field of Classification Search
  USPC ............ 340/539.11, 539.13, 539.12, 539.26, 340/573.1
  See application file for complete search history.

(56) References Cited

U.S. PATENT DOCUMENTS

| | | | |
|---|---|---|---|
| 2011/0273309 A1 | 11/2011 | Zhang et al. | |
| 2011/0310701 A1* | 12/2011 | Schuster | H04B 13/02 367/38 |
| 2014/0107932 A1* | 4/2014 | Luna | G01D 21/00 702/19 |
| 2015/0077737 A1* | 3/2015 | Belinsky | G01N 21/53 356/51 |
| 2016/0066848 A1* | 3/2016 | Klosinski, Jr. | A61B 5/6803 600/301 |

* cited by examiner

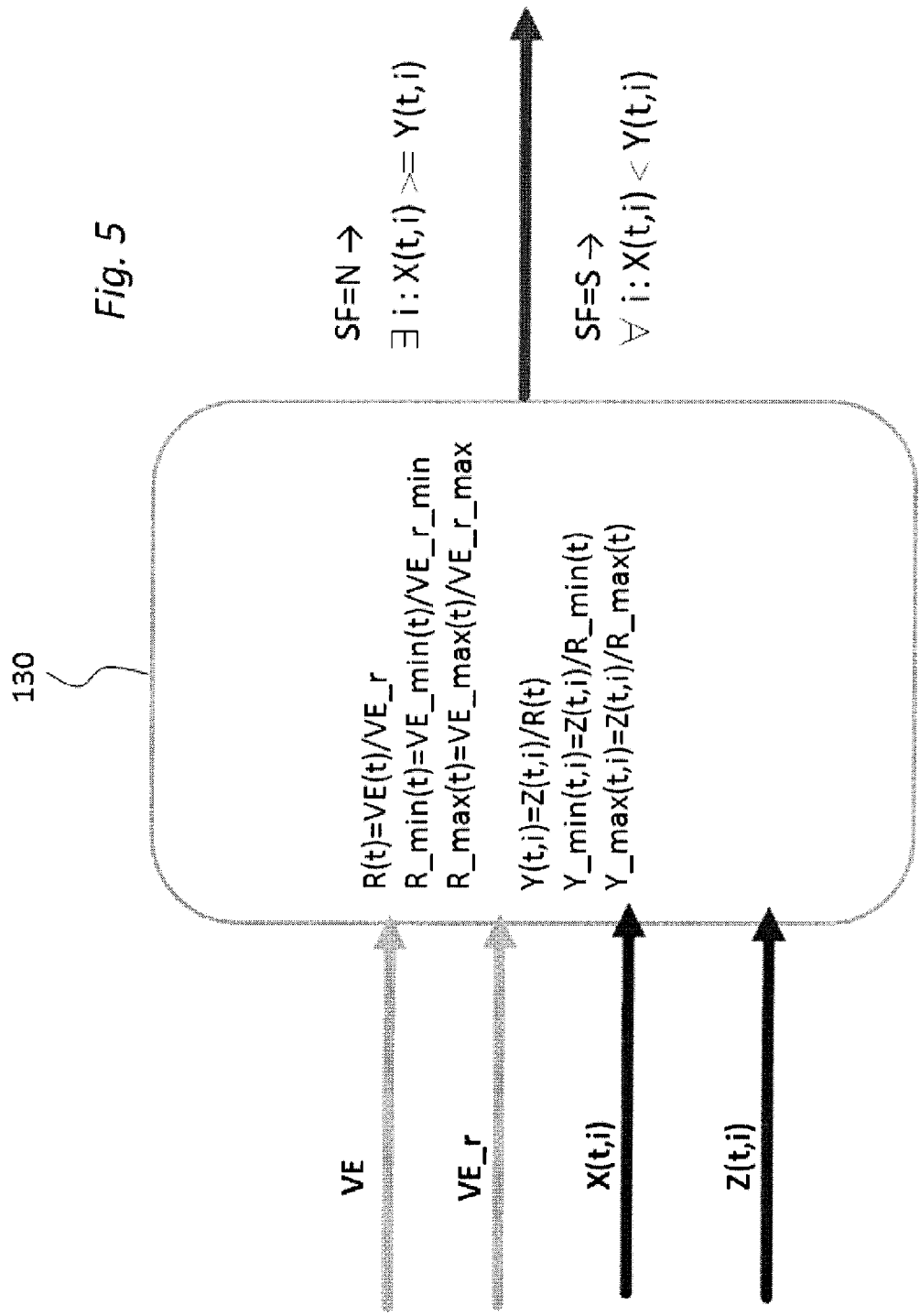

SYSTEM FOR SIGNALLING DANGER WARNINGS ARISING FROM EXPOSURE OF A SUBJECT TO ATMOSPHERIC POLLUTANTS, AND CORRESPONDING METHOD AND MOBILE DEVICE

CROSS REFERENCE TO RELATED APPLICATIONS

This application is a national stage filing under section 371 of International Application No. PCT/IB2014/058155, filed on Jan. 9, 2014, and published in English on Jul. 17, 2014, as WO 2014/108851 A1, and claims priority of Italian application No. TO2013A000022 filed on Jan. 11, 2013, the entire disclosure of these applications being hereby incorporated herein by reference.

FIELD OF THE INVENTION

The present invention relates to a system for signalling danger warnings arising from exposure of a subject to pollutants, in particular atmospheric pollutants, comprising: means for detecting environmental information in the proximity of the subject, at least one personal mobile terminal, sensor means associated to the subject, configured for detecting one or more physiological parameters of the subject and supplying them to said personal mobile terminal of the subject, means for detecting the position of the subject, and a data-processing module for determining said danger warning.

GENERAL TECHNICAL PROBLEM

It is in general known to monitor the conditions of pollution and to issue alarms if it is found that the values of the conditions of pollution (for example, the so-called, fine dust or particulate matter—PM) are dangerous for the subjects that are present in a given area.

From the Italian patent application No. RM2008A000499 there is known a mobile device with functions of monitoring of the environment and biometric data in vivo for detecting onset of anomalous conditions, which comprises a plurality of functional units, amongst which a unit dedicated to detection of environmental quantities, a unit dedicated to detection of physiological and biometric quantities, a unit dedicated to the geo-referenced position of the device or terminal itself, and a unit that is able to process the biometric, environmental, and space-time data, as well as to transmit them to an operating centre and/or to receive instructions therefrom.

The above mobile device, however, proves somewhat cumbersome, in particular for monitoring pollution, on account of the need to incorporate a multiplicity of sensors, especially a multiplicity of sensors for detecting pollutant agents. Reduction of the overall dimensions by limiting the number of sensors leads to a reduction of the agents detected and of the reliability of the system.

The object of the present invention is to overcome the drawbacks of the known art, in particular to provide a system for signalling danger warnings arising from exposure of a subject to pollutants, in particular atmospheric pollutants, comprising a personal mobile terminal of the subject that will present reduced overall dimensions and will at the same time enable a more reliable warning function than do known systems.

The object of the present invention is achieved by a system having the characteristics forming the subject of the ensuing claims, which form, an integral part of the technical, teaching provided herein in relation to the invention. The object of the invention is also a corresponding method and mobile device.

BRIEF DESCRIPTION OF THE DRAWINGS

The invention will now be described with reference to the annexed drawings, which are provided purely by way of non-limiting example and in which:

FIG. 5 is a schematic illustration of a third step of the method according to FIG. 2.

DETAILED DESCRIPTION OF THE INVENTION

In brief, the system for evaluating the danger for a subject of exposure to pollutants according to the invention comprises sensor means for detecting one or more physiological parameters of a subject, means for receiving information on the pollutants present in an area in which the subject is located, and processing means for calculating the danger of exposure to pollutants as a function of the aforesaid one or more physiological parameters and the aforesaid information on the pollutants present in an area in which the subject is located.

According to a main aspect of the invention, the information on the pollutants present in an area in which the subject is located are received by a network for detection of environmental information that covers a region comprising the area in which the subject is present.

Figure 1:
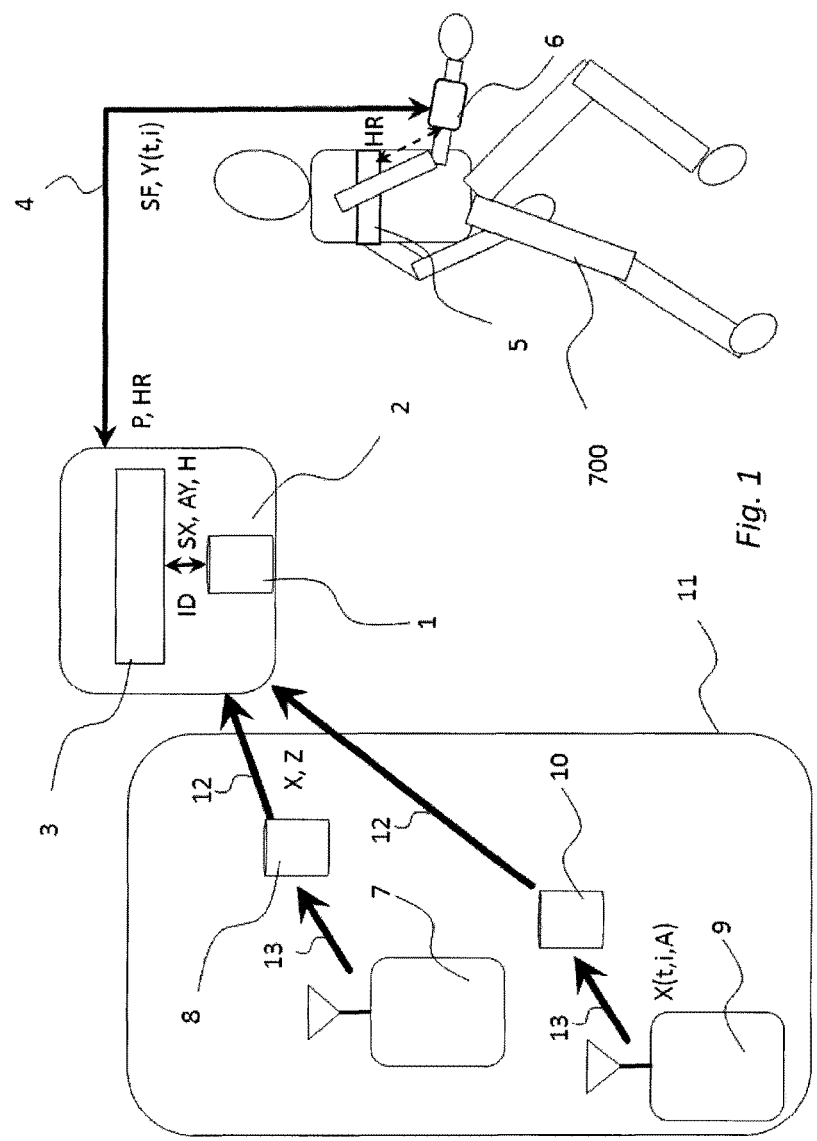
FIG. 1 is a principle diagram representing a system according to the invention.

Illustrated in FIG. 1 is the system according to the invention.

A subject 700 is represented, i.e., a user of the service implemented via the system according to the invention, who is practising a physical activity such as jogging and is wearing a sensor for detecting physiological parameters, represented in the example of embodiment by a chest strap 5 with heart-rate monitor that measures the heart rate HR of the subject 700, and a personal device 6 that can be worn preferably on the wrist or arm.

The above wearable device 6 is able to exchange data, in wireless or wired mode, for receiving the data measured by the sensor on the chest strap 5. When the subject 700 starts practising his sporting activity, whether in a competition, or simply training, the data, i.e., the physiological parameters of the subject 700, acquired by the chest strap 5, by means of the wearable device 6 are sent to a data-processing unit 2, in the example of embodiment illustrated herein set in a position remote from the wearable device 6 and in communication therewith through a communication channel 4, in particular a communication channel of a mobile-phone network. In this data-processing unit 2, the physiological parameters of the subject are set in relation with the concentrations of pollutants $X(t, i)$ measured by a network 11 of air-quality monitoring units and with the personal data of the subject 700, provided during configuration of the service implemented by the system according to the invention.

The result of the aforesaid processing by the data-processing unit 2 is a warning of danger SF as a function of the physical activity practised in a given time frame, in particular at a given instant t, which is sent back to the wearable device 6 so that the subject 700 can be informed thereof. The subject 700 is thus informed about the danger of the pollutant substances potentially inhaled during ventilation in situations of physical exercise, by displaying indices or symbols of danger or issuing alarms as a function of the values of the above indices of danger.

The time instant t corresponds to the instant of acquisition of the physiological parameters. In what follows, reference will be made to a real-time evaluation, whereby is meant that given a measurement of physiological parameters, such as heart rate at the instant t, the system acquires in a practically simultaneous way the position information, and, with the times of propagation linked to the communications and to the operations performed by the processors, retrieves the environmental information available at that moment in the environmental database and regarding a time window in which the instant t is included.

The aforesaid danger warning SF in one embodiment comprises a signal with two values or symbols, which represent the state of healthiness or unhealthiness of the area in which the subject is present 700 as a function of the physical activity practised by him at a given, instant t.

In other embodiments, the aforesaid danger warning SF may comprise values of toxicity of the pollutant i at the instant t, Y(i, t) corresponding, i.e., set in relation, to the physical activity of the subject 700.

According to various embodiments the danger warning SF may assume, according to the requests of the user, also one or more of the following forms:

an alarm warning of overstepping of given thresholds of pollutant in absolute value;

display of the absolute levels of each pollutant present in the area;

the historic recording of the activities performed by the user (time, course, position) and of the amount of pollutant absorbed in time;

indications on the areas located in the proximity of the user with lesser or greater presence of pollutants;

data regarding forecasts of presence and dispersion of the pollutants taking into account temperature, rainfall or snowfall, wind, humidity, and solar radiation.

Some of the above warnings can be likewise signalled separately, for example upon request of the user.

It should be noted that the aforesaid data-processing unit 2 can be set even locally on the subject 700, in particular in the wearable device 6, sharing for example the transceiver means thereof, i.e., in particular means for transceiving on the communication channel 4 and exchanging data with a network 11 of air-quality monitoring units and other possible networks.

The system according to the invention hence basically comprises:

a personal device 6, in particular one that can be worn by the subject 700, connected to at least one sensor of physiological parameters of the subject 700, in particular a chest strap 5 that detects the heart rate HR; in various embodiments, a plethysmograph may alternatively or additionally be present for detection of the ventilation rate and/or an oxypulsimeter (or oxymeter) for detecting the bound haemoglobin;

a data-processing unit 2 configured for retrieving information on pollution geo-referenced by a network 11 of air-quality monitoring units.

The network 11 of air-quality monitoring units comprises a plurality of public monitoring units 9 and/or of private monitoring units 7, which contain transducers sensitive to the concentration of pollutant substances present in the environment where they are installed. The aforesaid air-quality monitoring units 7 and/or 9 are connected to a second communication network 12, which is in the example the Internet, exploiting mobile-radio communication networks 13, for example GPRS, UMTS, HSDPA, LTE, or else even wired connections. The measurements of pollutant parameters acquired by the aforesaid plurality of monitoring units 7 and/or 9 are periodically recorded and made available in respective environmental databases 8 or 10, which are also connected to the Internet 12, and thus have the possibility of receiving the measurements of the aforesaid plurality of monitoring units 7 and/or 9.

The monitoring units 7 and/or 9 are located in a scattered way over the territory in respective areas of coverage A. Each monitoring unit 7 and/or 9 covers a respective area A, acquiring data on concentration of pollutants of a given type i considered at a given instant t, i.e., X(t, i), in the aforesaid area A. The data of concentration of pollutants measured by each air-quality monitoring unit. are thus designated by X(t, i, A). The set of the aforesaid areas A identifies the region of coverage of the network 11 of air-quality monitoring units.

The air-quality monitoring units may be either stations for acquisition of environmental data, owned by public bodies, in the case of public monitoring units 9, or purposely designed monitoring units that can be installed in private areas, in the case of private monitoring units 7. Consequently, the system according to the invention is able to exploit the pollution data detected by purposely provided air-quality monitoring units installed in private areas, whether indoor or outdoor. The aforesaid monitoring units 7 and/or 9 send the data on concentration of pollutants of a given type i considered at a given instant t, i.e., X(t, i), in a given area A to the environmental database 8, or respectively 10, which in turn makes available the aforesaid data, together with the information on the region or area in which they have been detected, for their retrieval and processing by the data-processing unit 2, which is connected to the second network 12 itself, in particular the Internet. It is likewise possible to use the data coming from air-quality monitoring units owned by public bodies accessible through the Internet 12.

As has been mentioned, the subject 700 wears a chest strap 5 comprising a sensor capable of detecting the heart rate HR and possibly also a sensor that detects the breathing rate. The breathing rate may be detected, for example, via a plethysmograph integrated in the chest strap 5. The chest strap 5 is connected, in the example illustrated in FIG. 1, via radio with a standard short-range wireless protocol on the 2.4-GHz ISM frequency band, to the wearable device 6.

The wearable device 6 comprises transceiver modules designed to communicate with the chest strap 5 and to exchange data on a mobile communication network, which, as has been said, in the example of FIG. 1, corresponds to the communication channel 4. The wearable device 6 preferably further comprises a touch screen for interaction with the subject 700. The above wearable device 6 can be worn strapped on any part of the upper or lower limbs. The wearable device 6 may be a mobile phone, a so-called smartphone, for example an iPhone, or a similar transceiver apparatus for mobile and short-range network, with processing capacity, and a user touch interface or in any case an interface suited to enabling simple interactions for a subject who is prevalently moving.

The wearable device 6, acquires from the chest strap 5 a physiological parameter such as the heart rate HR and/or the breathing rate, forwards this to the data-processing unit 2, exploiting a secure and encrypted communication channel 4, for example on the cellular mobile-radio network GPRS or UMTS or HSDPA or LTE, together with information regarding identification of the subject 700 who is using the system and a position P thereof detected via locating systems, for example a position sensor, preferably a GPS one. Also the aforesaid position sensor is in the example incorporated in the mobile phone that functions as wearable device 6, even though if could alternatively be a position sensor separate from the aforesaid wearable device 6.

The wearable device 6 then receives from the data-processing unit 2 the result of a calculation that sets in relation the physiological parameter HR acquired, the concentrations of pollution X(t, i) of the area A in which the physical activity of the subject 700 is being carried out, and personal data of the subject 700, for example the sex of the subject. On the screen of the wearable device 6 there is then issued to the subject 700 a danger warning SF as a function of the physical activity practised at the instant t, possibly accompanied by the corresponding values of toxicity of the pollutant at the instant t, i.e., Y(i, t). There may also possibly be issued information on the amount of pollutants introduced into the organism, through ventilation during physical activity.

The data-processing unit 2 is at the centre of the system, acquires the data from the environmental databases 8, 10 of the air-quality monitoring units 7 and 9, receives the information on the individual active users or subjects 700, processes the responses in terms of danger warnings, and sends them to the aforesaid active users 700. In the preferred embodiment, the aforesaid processing unit 2 comprises a server unit 3 and a local database 1. The server unit 3 handles the connections to the active users 700 via respective secure communication channels 4 of wireless communication networks. Possibly, the mobile-phone network can function as medium for connection to the server 3 of the personal device 6 through access to the Internet, by means of interfaces of an http socket type, or services (web services) with REST or SOAP access, and provides the measurement-processing service. The local database 1 of the unit 2 is configured for recording personal information on the individual subjects 700, users of the service implemented by the system according to the invention, such as for example the sex, age, height, as well as possibly demographic data and data regarding management of the user's subscription to the service. Processing of the responses is carried out by the server unit 3, which in one embodiment is configured for:

accepting and managing, on the secure communication channel 4 and possibly on the Internet, connection of the active user 700 who is starting his physical activity;

recognizing an identifier ID of the active subject 700;

retrieving in the local database 1 personal information, for example the sex SX, corresponding to the identifier ID of the active subject 700;

acquiring the position P supplied by the corresponding wearable device 6 for locating the active subject 700; and retrieving, on the basis of the aforesaid position P of the active subject 700, the data X(t, i, A) on concentration of the pollutants of a given type i considered at the instant t, regarding the state of pollution of the area A in which the active subject 700 is present, on the basis of the position P supplied by the wearable device 6, obtaining the aforesaid pollution-concentration data X (t, i, A) from the environmental database 8 and/or 10, which in turn receive the data from the monitoring units 7 and/or 9 nearest to the place in which the active user 700 is practising the sporting activity;

acquiring in real time the physiological data of the subject 700; these physiological, data, which comprise, for example, the height, age, and sex of the subject, may be acquired once again from the local database 1 itself, where they have been recorded, or else from an external data structure, for example supplied on the communication channel 4 by the wearable device 6;

processing in real time the aforesaid physiological data of the subject 700, setting them in relation with the measurements of concentration X (t, i, A) of pollutants in the area A where the subject 700 is practising the physical activity; and transmitting in real time on the secure communication channel 4 the result of the processing to the wearable device 6 of the active user 700 who is practising the physical activity.

Figure 2:
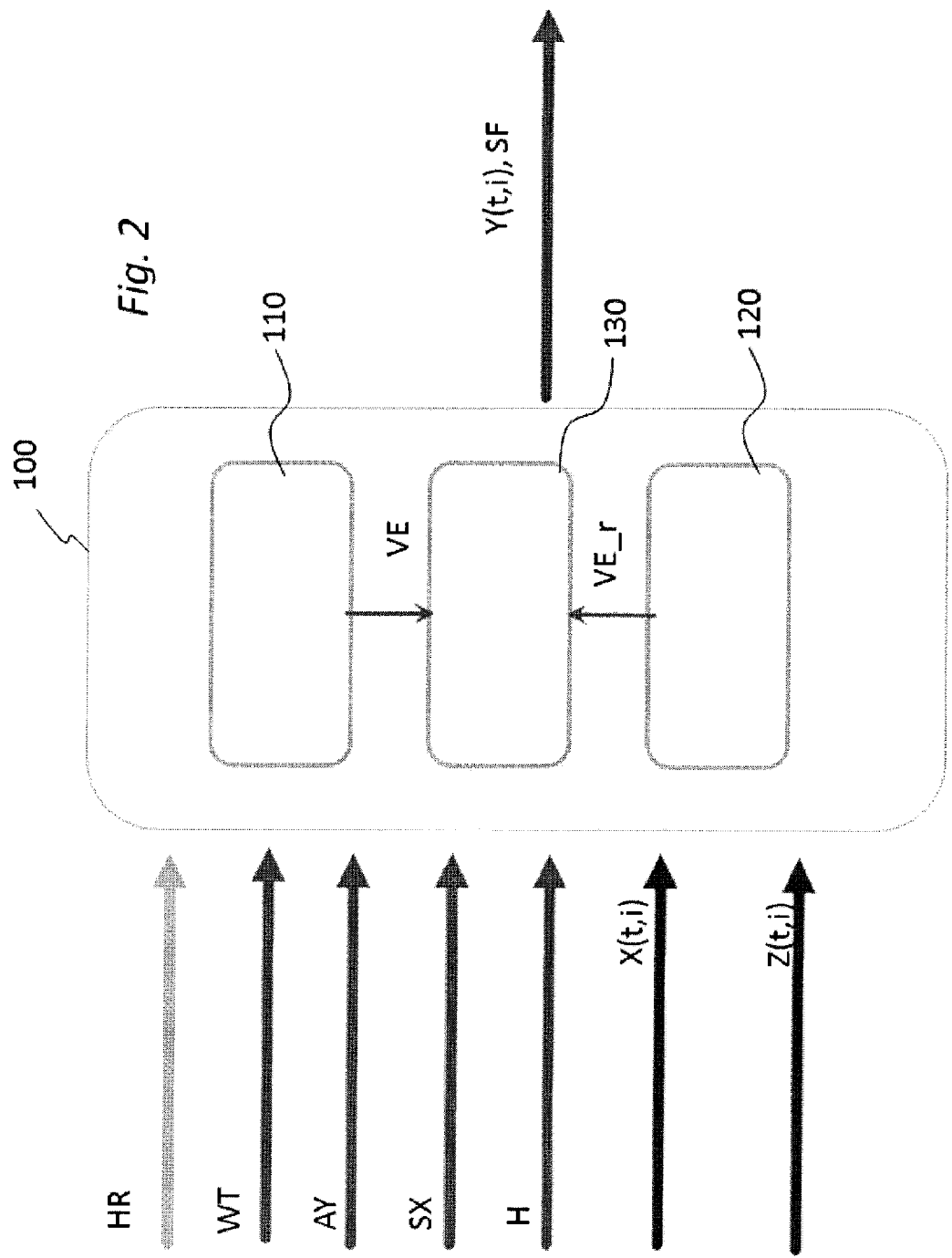
FIG. 2 is a schematic illustration of a method implemented by the system according to the invention.

Represented in FIG. 2 is a general diagram of the model for processing danger indices implemented in the processing unit 2, designated as a whole by the reference number 100.

The above processing model 100 has a plurality of input variables that comprise:

the heart rate of the subject 700 at a given instant t, HR(t), expressed in b.p.m. (beats per minute);

the sex SX of the subject 700, male or female;

the concentration of the pollutants i of a given type considered at the instant t measured in the area A, i.e., X(t, i, A), expressed in $mg/m^3$, or $\mu g/m^3$ in other cases; the type i may indicate, for example, fine dust PM.

the thresholds of toxicity of the concentration of each pollutant i, i.e., Z.(i), expressed in $mg/m^3$, or $\mu g/m^3$ in other cases; these parameters preferably reflect the ones indicated in the World Health Organization (WHO) "Air Quality Guidelines for Europe"—second edition.

In the embodiment illustrated, the model for processing danger indices 100 also receives further morphological parameters that are characteristic of the subject:

the age AY of the subject 700, in years;

the height H of the subject 700, in the example expressed in cm;

the weight WT of the subject 700, in the example expressed in kg.

Figure 3:
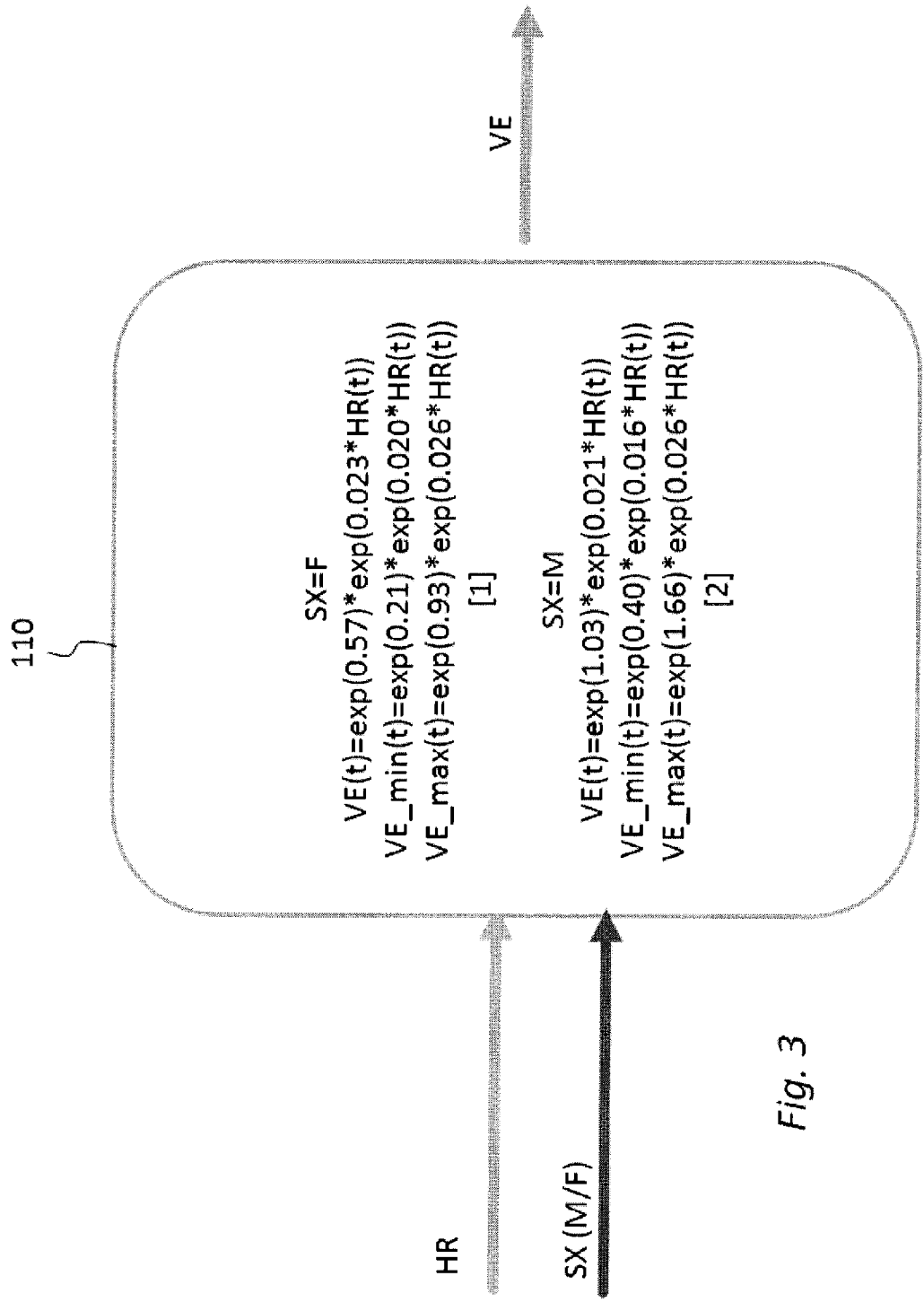
FIG. 3 is a schematic illustration of a first step of the method, according to FIG. 2.
Figure 4:
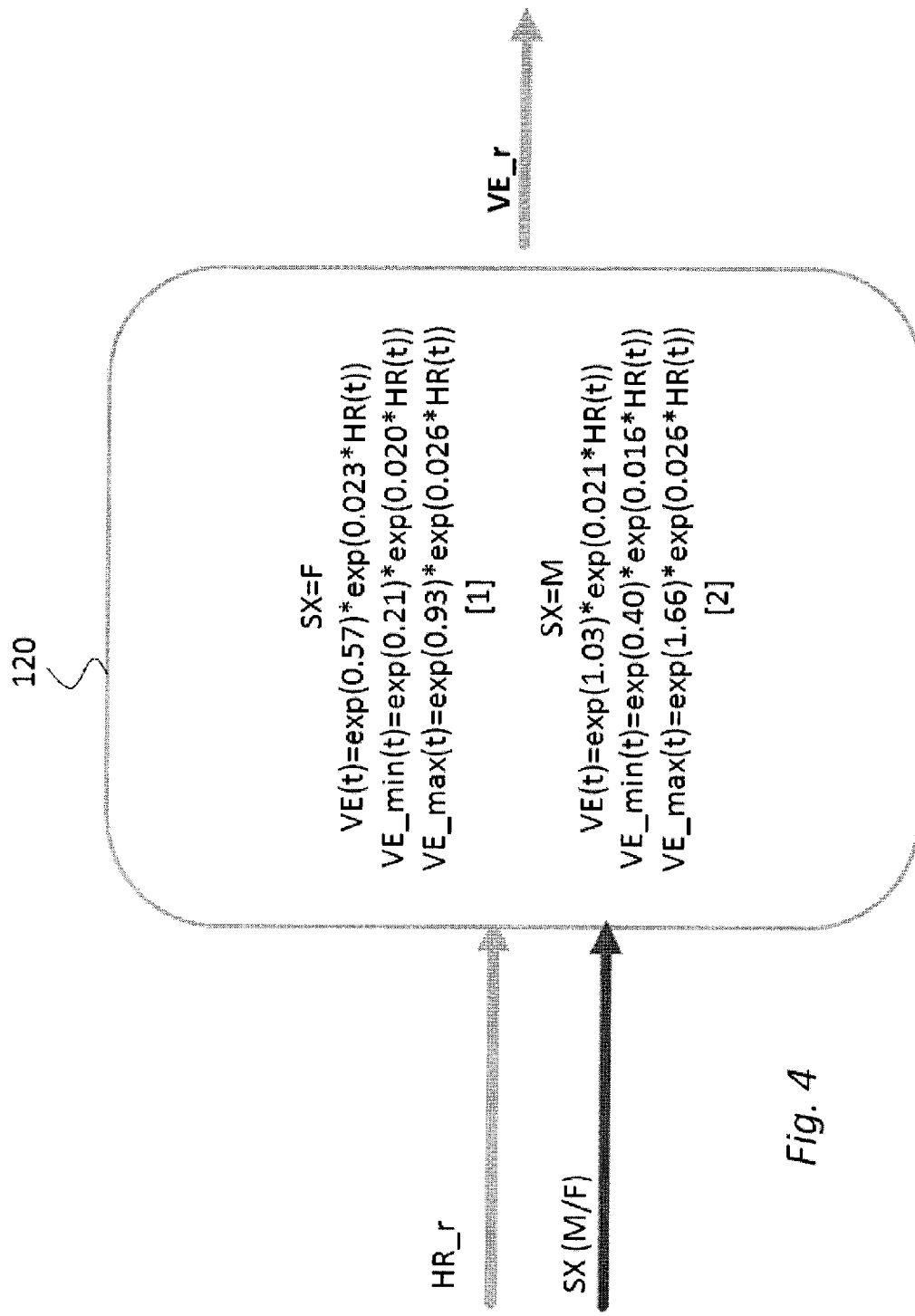
FIG. 4 is a schematic illustration of a second step of the method according to FIG. 2.

The aforesaid further morphological parameters are not directly used in the model illustrated as preferred embodiment with reference to FIGS. 3, 4, and 5 but can be used in possible alternative models, for example also for providing the user with information regarding his own EMI (Body Mass Index).

The model for processing danger indices 100 comprises three processing sub-modules 110, 120, 130 that will be illustrated with reference to FIGS. 3, 4, and 5, respectively.

The output variables of the model 100 in the example represented herein comprise:

a threshold of toxicity of each pollutant i at the instant t, i.e., Y(t, i), as a function of the activity of the subject 700; and a danger warning SF, i.e., preferably a signal with two values or symbols, which represent a state of healthiness or unhealthiness of the area in which the subject 700 is present as a function of the physical activity being practised by him at the instant t.

According to the example of embodiment, the processing unit 2 signals the aforesaid danger warning SF to the wearable device 6, which displays it for the subject 700 or issues an alarm, according to the value of the aforesaid danger warning SF. According to various embodiments, the processing unit 2 can either signal danger warnings SF or the values of threshold of toxicity of each pollutant i at the instant t, Y(t, i), which are set in relation to the activity of the subject 700 and to the area A in which he is present in such a way that also these values can be either displayed or used for further processing.

Illustrated in detail in FIG. 4 is the processing sub-module 110, which is configured for calculating ventilation VE of the active subject.

The processing sub-module 110 receives at input:
the heart rate of the subject 700 at the instant t, i.e., HR(t), expressed in b.p.m.; and
sex SX of the subject 700;
and supplies at output:
the estimate of the ventilation at the instant t, i.e., VE(t), expressed in l/min as a function, of the heart rate HR and sex SX.

The processing sub-module 110 estimates the ventilation VE at the instant t starting from the sex SX of the subject 700 and his heart rate. The estimation described in Zuurbier, Hoek, van den Hazel and Brunekreef, "Minute ventilation of cyclists, car and bus passengers: an experimental study", Environmental Health 2009, 8: 48, is preferably used. In particular:

for women (SX=F) the following relation is used:

$$VE(t)=\exp(0.57)*\exp(0.023*HR(t)) \quad (1)$$

with confidence interval defined by the minimum $VE\_min(t)=\exp(0.21)*\exp(0.020*HR(t))$ and by the maximum $VE\_max(t)=\exp(0.93)*\exp(0.026*HR(t))$;

for men (SX=M) the following relation is used:

$$VE(t)=\exp(1.03)*\exp(0.021*HR(t)) \quad (2)$$

with confidence interval defined by the minimum $VE\_min(t)=\exp(0.40)*\exp(0.016*HR(t))$ and by the maximum $VE\_max(t)=\exp(1.66)*\exp(0.026*HR(t))$.

The processing sub-module 110 needs to be calibrated with respect to each subject 700, the calibration being performed by the processing sub-module 120 illustrated in FIG. 4. It is envisaged in fact to record the heart rate at rest HR_r of the subject 700. Starting from the aforesaid heart rate at rest HR_r, a ventilation at rest VE_r is estimated using the relations (1) and (2) with the corresponding confidence intervals. Consequently, for example, in the case of the relation (1) for women, the ventilation at rest VE_r is $VE\_r(t)=\exp(0.57)*\exp(0.023*HR\_r(t))$, where HR_r is the heart rate at rest.

In the processing sub-module 130, described in detail in FIG. 5, the values of the active subject 700 and of the subject 700 at rest are then compared in order to compute the danger index SF.

At each instant of use t, a ratio R(t) between the estimated ventilation VE(t) and the ventilation at rest of the user VE_r is then calculated, along with a corresponding confidence interval. In particular:

$$R(t)=VE(t)/VE\_r \quad (3)$$

and the confidence interval of the ratio R(t) ranges between a minimum value $$R\_min(t)=VE\_min(t)/VE\_r\_min \quad (4)$$

and a maximum value $$R\_max(t)=VE\_max(t)/VE\_r\_max \quad (5)$$

The aforesaid ratio R(t) describes how much the physical activity of the user 700 at the instant t increases ventilation with respect to the ventilation at rest. The aforesaid increase in ventilation hence manifests itself in a proportioned increase of the introduction of pollutants into the organism as compared to when the individual is at rest. Consequently, the threshold of toxicity of each pollutant i at the instant t, taking into account this increase, is estimated as follows $$Y(t, i)=X(t, i)/R(t) \quad (6)$$

with a confidence interval that ranges between a minimum $$Y\_min(t, i)=Z(i)/R\_min(t) \quad (7)$$

and a maximum $$Y\_max(t, i)=Z(i)/R\_max(t) \quad (8)$$

With the model of Eqs. (1)-(7) and similar models, in practice, the toxicity threshold Y(t, i) decreases approximately according to a decreasing exponential function of the difference between the heart rate measured during the sporting activity HR and the heart rate measured at rest HR_r.

The warning SF of environmental danger as a function of the physical activity practised at the instant t is represented as follows :

'unhealtiness', or danger, at the instant t if for at least one pollutant the following condition is found: $X(t, i) \geq Y(t, i)$;

'healthiness', or safety, at the instant t if for each pollutant the following condition is found: $X(t, i) < Y(t, i)$; if the danger warning SF is considered as a variable, for example, SF is set equal to N, i.e., negative warning.

As has been said, this danger warning SF can be supplied in the form of a code with two values, whether these be numeric values, logic values, or even strings in text format. Indicated in the figures are, for example, SF=N, i.e., negative warning for healthiness, and SF=Y for safety.

The wearable device 6 is configured for receiving at least the aforesaid danger warning SF and for signalling to the subject at least the aforesaid danger warning SF, which indicates danger or absence of danger, or else issuing alarms as a function of the values of the aforesaid warning SF, for example through the speaker of the mobile phone.

In various embodiments, the processing sub-module 110 can receive at input also morphological information regarding the height H, age AY, and weight ???WT [?MANCA] of the subject for evaluating the slope of the ratio between the assumption of oxygen, and the logarithm of the ventilation according to relations such as, for example, the ones studied by Sun et al. (Oxygen uptake efficiency plateau: physiology and reference values—2012).

$$OVE=-0.610-0.032*AY+0.023*H+0.008*WT \quad (SX=M)$$
$$OVE=-1.178-0.032*AY+0.023*H+0.008*WT \quad (SX=F)$$

OVE expresses the ratio between the assumption of oxygen, which can be for example detected, by way non-limiting of example, via a plethysmography for detection of the ventilation rate, and the logarithm of the ventilation VE, and is here expressed in L/min/log(L/min).

In this regard, it is to be noted that in possible variant embodiments the height H of the subject can be recorded also to take into account the mechanisms of turbulence at the basis of dispersion of pollutants that are affected by the distance from the ground.

Hence, the characteristics and the advantages of the invention emerge clearly from the foregoing description.

Of course, the details of construction and the embodiments may vary widely with respect to what has been described and illustrated herein, without thereby departing from the sphere of protection of the present invention, as defined in the annexed claims.

In preferred embodiments, the personal device is a device that can be worn, this affording the advantage of a convenient portability for the subject who is practising activity. However, in general, where there arise the conditions, the personal device may not be worn; for example, it may be carried in the hand. Furthermore, it is emphasized how the wearable device may be a personal device, such as a smartphone, rendered wearable via the addition, in a removable way, of straps or wrist-bands. In possible variant embodiments, also the data-transmission unit may be separate from the personal device.

According to a variant, the processing unit 2 instead may, on the basis of the environmental databases of the air-quality monitoring units, supply information on the toxicity thresholds, once again set in relation to the physiological activity of the subject also for areas neighbouring upon the ones where the aforesaid subject is present. In particular, the processing unit 2, on the basis of the values of the aforesaid toxicity thresholds, can provide the subject with information for navigation into areas with lower toxicity thresholds.

The environmental pollutants that can be measured comprise carbon monoxide, sulphur dioxide, metals, such as lead, arsenic, cadmium, or nickel, benzene, nitrogen dioxide, ozone, particulate matter (PM10, PM5, PM2, 5).

The physiological parameters that are acquired may comprise heart rate, pulmonary ventilation, oxygen, saturation.

The morphological parameters that are recorded or acquired may comprise age, weight, height, and sex, and it is possible to envisage deriving the body mass index or the instantaneous caloric consumption or the caloric consumption during the activity, in addition to other derived parameters, such as the effectiveness of training.

The system may moreover envisage environmental sensors, set in the monitoring units or on the subject, which measure parameters amongst which humidity, temperature, altitude, exposure to ultraviolet radiation, atmospheric pressure.

The system may, on the basis of the position information, calculate and supply geographical parameters, such as speed of displacement of the subject, distance covered, etc.

As has been described, in various embodiments, as an alternative or in addition to the heart-rate monitor that measures the heart rate, there may be present a plethysmography for detection of the ventilation rate and/or an oxypulsimeter (or oxymeter) for detection of bound haemoglobin. These physiological parameters also enable, in fact, calculation of the ventilation and absorption of pollutants at a given instant for the active subject.

It should moreover be noted that in general the invention is not exclusively aimed at physiological parameters that enable calculation of ventilation and the corresponding absorption of pollutants, but also at any physiological parameter suitable for calculating in the data-processing module danger warnings as a function of the environmental information and of the local-detection data, which comprise the aforesaid physiological parameters of the subject and the position of the subject in the system according to the invention.

The invention claimed is:

1. A system for signaling danger warnings arising from exposure of a subject to pollutants, in particular atmospheric pollutants, comprising:
   means for detecting environmental information in the proximity of the subject;
   at least one personal mobile terminal;
   sensor means associated to the subject, configured for detecting one or more physiological parameters of the subject and supplying the parameters to said personal mobile terminal of the subject;
   means for detecting the position of the subject; and
   a data-processing module for determining a danger warning,
   said mobile terminal configured for sending to said data-processing module local-detection data corresponding to the subject, comprising said one or more physiological parameters of the subject, together with the corresponding position of the subject; and
   said data-processing module configured for retrieving, as a function of said position of the subject, environmental information from a network for detection of environmental information, comprising said means for detecting environmental information, which covers a region comprising an area in which said position of the subject is located,
   said personal mobile terminal being configured for:
   receiving from said data-processing module danger warnings arising from exposure to pollutants calculated in said data-processing module as a function of said environmental information and of said local-detection data, comprising said one or more physiological parameters of the subject and said corresponding position of the subject; and
   said danger warnings calculation comprising:
   calculating a ratio of the ventilation of the active subject at a given time instant from said one or more physiological parameters and a ventilation of the subject at rest calculated on the basis of said one or more physiological parameters,
   estimating a toxicity threshold of a pollutant at the given time instant as a function of said ratio and of a toxicity threshold,
   evaluating a danger warning of the environment indicating danger if a measured concentration of the pollutant is higher than said estimated toxicity threshold,
   displaying to the subject said danger warnings or issuing alarms as a function of the values of said danger warnings.

2. The system according to claim 1, wherein said personal mobile terminal can be worn by the subject.

3. The system according to claim 1, wherein said data-processing module is set remote from the personal mobile terminal and in connection with said personal mobile terminal through a communication network.

4. The system according to claim 1, wherein said data-processing module is set locally with respect to the personal mobile terminal.

5. The system according to claim 1, wherein said one or more physiological parameters of the subject comprise the heart rate of the subject.

6. The system according to claim 1, wherein said one or more physiological parameters of the subject comprise the breathing rate of the subject and/or the bound haemoglobin.

7. The system according to claim 1, wherein said data-processing module is configured for supplying to said personal mobile terminal information on the danger of neighboring geographical areas and/or navigation information as a function of a danger index of the neighboring areas.

8. The system according to claim 1, wherein said data-processing module is configured for:
   acquiring personal data, in particular morphological data of the subject; and calculating in said data-processing module said danger warning arising from exposure to pollutants as a function of said personal data, in particular, morphological data of the subject and as a function of said environmental information and of said local-detection data, comprising said one or more physiological parameters of the subject and said corresponding position of the subject.

9. The system according to claim 8, wherein said data-processing module is configured for accepting and managing the connection of the personal terminal of a subject, recognizing an identifier of the active subject, and retrieving in a database of the data-processing module personal information, comprising said personal data, in particular morphological data, corresponding to the identifier of the subject.

10. The system according to claim 8 wherein it is configured for:
calculating the ventilation of the active subject at a given time instant as a function at least of the heart rate and of the sex of the subject;
comparing the ventilation of the active subject at a given time instant with a ventilation at rest calculated on the basis of a heart rate at rest of the subject recorded, in particular recorded in the processing unit together with said personal data, in particular morphological data, by calculating a ratio between the estimated ventilation, and the ventilation at rest of the user and
estimating a toxicity threshold of each pollutant at the given time instant as a function of said ratio and of a toxicity threshold.

11. The system according to claim 10, wherein it is configured for evaluating a danger warning of the environment as a function of the physical activity practiced at the given time instant, indicating danger if for at least one pollutant it is found that the concentrations of pollutants measured are higher than said estimated toxicity threshold.

12. A personal mobile terminal for signaling danger warnings arising from exposure of a subject to pollutants, configured for operating in the system according to claim 1.

13. A method for signaling danger warnings arising from exposure of a subject to pollutants, in particular atmospheric pollutants, comprising:
detecting environmental information in the proximity of the subject,
detecting one or more physiological parameters of the subject and supplying them to a personal mobile terminal of the subject,
detecting the position of the subject, and
processing said environmental information and one or more physiological parameters of the subject,
retrieving, as a function of said position of the subject, environmental information from a network for detection of environmental information, configured for detecting environmental information in a region comprising an area that includes said position of the subject;
receiving on said personal mobile terminal danger warnings arising from exposure to pollutants, calculated as a function of said local-detection data, comprising said one or more physiological parameters of the subject and said corresponding position of the subject; and
calculating a ratio of the ventilation of the active subject at a given time instant from said one or more physiological parameters and a ventilation of the subject at rest calculated on the basis of said one or more physiological parameters,
estimating a toxicity threshold of a pollutant at the given time instant as a function of said ratio and of a toxicity threshold,
evaluating a danger warning of the environment indicating danger if a measured concentration of a pollutant is higher than said estimated toxicity threshold,
displaying to the subject said danger warnings or issuing alarms as a function of the values of said danger warnings.

14. The system according to claim 4, wherein said module is located in said terminal.

* * * * *